Figure 1:
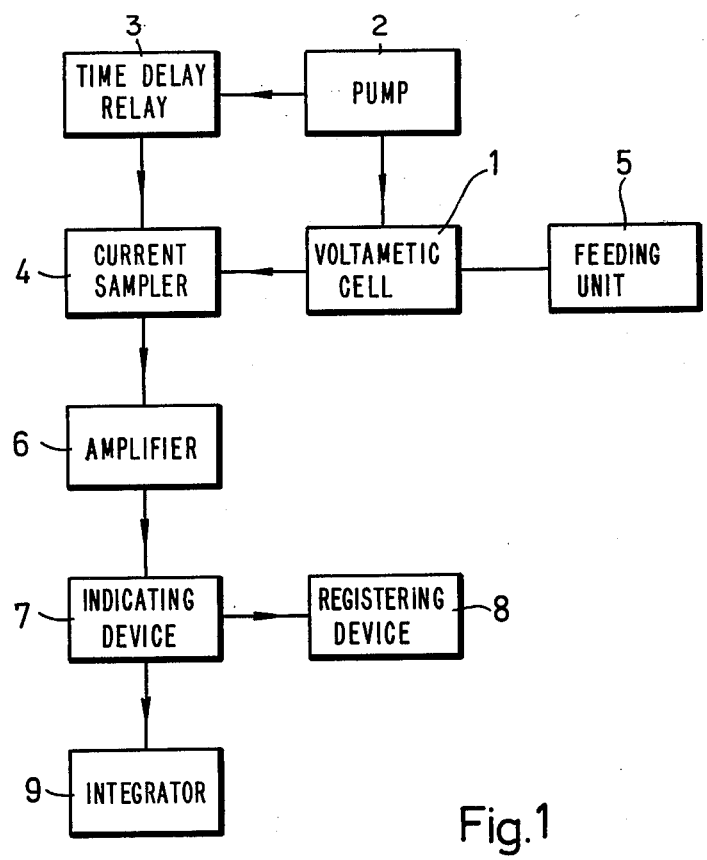

United States Patent [19]

Pungor et al.

[11] 4,066,406

[45] Jan. 3, 1978

[54] PROCESS AND APPARATUS FOR THE VOLTAMMETRIC MEASUREMENT OF THE QUANTITY OR MASS OF SEPARATED SAMPLE COMPONENTS

[75] Inventors: Ernö Pungor; Mária Váradi, both of Budapest, Hungary

[73] Assignee: Labor Muszeripari Muvek, Esztergom, Hungary

[21] Appl. No.: 677,389

[22] Filed: Apr. 15, 1976

[30] Foreign Application Priority Data

Apr. 22, 1975 Hungary ............................... LA 863

[51] Int. Cl.² .................... G01N 27/26; G01N 27/30; G01N 31/08
[52] U.S. Cl. ................................ 23/230 R; 23/253 R; 73/61.1 C; 324/71 R; 204/1 T; 204/195 R
[58] Field of Search ................. 23/230 R, 253 R, 259; 73/61.1 R, 61.1 C; 210/31 C; 324/71 R; 204/1 T, 195 R

[56] References Cited

U.S. PATENT DOCUMENTS 3,352,643   11/1967   Ando et al. ......................... 23/253 X
3,902,848   9/1975   Juvet, Jr. ............................. 23/253 X Primary Examiner—R.E. Serwin

[57] ABSTRACT

A process and apparatus for the voltammetric measurement of sample component quantities is disclosed wherein the material to be measured is passed by means of a pulsating-delivery pump into a voltammetric cell by way of a flow cross-section restriction to the surface of the voltammetric electrode, the liquid jet being adjusted such that its cross-section in the vicinity of the measuring surface of the electrode should be greater than the measurement area of the latter. The obtained voltammetric current curve is integrated at the area below the peak value, the current changing as a function of the pulsating flow rate of the liquid and the material quantities are determined from the integrated data. Preferably, the integration is effected from a value corresponding to 50% of the maximum flow rate to the maximum value and from there again down to 50% of the flow rate maximum.

3 Claims, 2 Drawing Figures

U.S. Patent        Jan. 3, 1978        4,066,406

PROCESS AND APPARATUS FOR THE VOLTAMMETRIC MEASUREMENT OF THE QUANTITY OR MASS OF SEPARATED SAMPLE COMPONENTS

The invention concerns a process for the voltammetric measurement of the amount or mass of separated sample components, wherein the material or substance to be measured is passed into a voltammetric measuring cell with the aid of a pump, and more particularly via a restriction or reduced cross-section to the surface of the voltammetric electrode and the quantity is determined by measuring the voltammetric current. The invention also concerns apparatus for carrying out the process.

As is known, liquid chromatography is used to measure the very small quantities or masses of sample components after separation. In the known process detectors are used which operate on the principle of measurement of the refractive index or light absorption and which have enabled measurement or detection taking place in the range of $10^{-10} - 10^{-11}$ Mol. For these purposes, the use of the ultra-sensitive detectors causes serious technical difficulties as regards their construction and the processing of the output signal representative of the detected quantity. A liquid chromatography measuring cell is known which is capable of detecting with the same sensivity as the above but which operates on electro-chemical principles under far simpler technical conditions. In this voltammetric cell a jet flow is established perpendicularly to the surface of the electrode and the liquid conveyed by means of a pump is passed pulsatingly to the electrode. The current output of the measuring cell is averaged and on the other hand the area of the individual liquid chromatography peaks are integrated In this known construction the problem also arises that the sensitivity cannot be increased beyond a certain value.

An aim of the invention is the obviation or mitigation of the above described drawbacks and the provision of a measurement process and apparatus with which ultra-high sensitivity and accurate measurement can be ensured with very simple technical means. The invention based on the discovery that these aims can be attained, i.e. the sensitivity of measurement can be increased, if a jet of liquid flow is formed wherein the cross-section of the jet is greater than the surface area of the electrode in the region of that electrode surface. The sensitivity, and thus accuracy, of the measurement can be increased still further in the case of pulsatingly conveyed liquid (i.e. liquid flowing at variable speed) if the current measurement takes place at the range of maximum speed, i.e. the peak current area is integrated and the quantity of material is determined from that.

The invention is therefore a process for the voltammetric measurement of sample component quantities, comprising providing pump means having a pulsating delivery, a voltammetric cell, an inlet in said cell including a flow cross-section restrictor, and a measurement electrode and integrating means; passing the material to be measured into the voltammetric cell and adjusting the cross-section of the liquid to a jet having a cross-section in the vicinity of the measuring surface of the electrode greater than the measurement area of the latter, and integrating the obtained voltammetric current curve at the area around the peak current value, and determining the material quantities from the integrated data.

It has been shown to be expedient to integrate the current value from 50% to the maximum of the flow rate and from there again in the flow rate decreasing sense to 50% of the peak value, and to determine the quantity of the material from these data.

The apparatus for carrying out the process according to the invention essentially consists in that the liquid conveying pump is a pulsating output or delivery pump which is electrically connected with a time delay relay and the latter is electrically connected to a current sampling device which passes the current depending on the concentration of the material delivered to the voltammetric cell to an indicating and/or recording or registering device.

Figure 2:
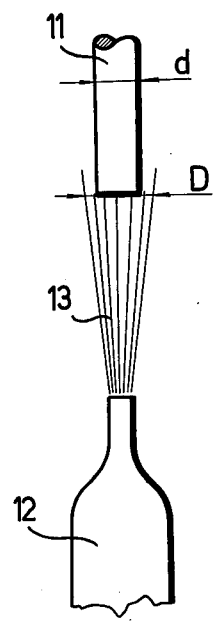

The invention is described in greater detail and by way of example only with reference to the accompanying drawing, wherein:

FIG. 1 is a schemmatic block diagram of the apparatus to illustrate the principle of the invention, and FIG. 2 is a fragmentary view of the voltammetric measuring cell in the region of the measuring electrode and the jet of liquid to be measured.

The apparatus according to the invention illustrated in FIG. 1 consists of a voltammetric cell 1 into which the liquid to be measured is conveyed by a pump 2. The pump 2 is electrically connected with a time delay relay 3 which is in turn connected to a current sampler 4. The current sampler 4 is, of course, electrically connected with the voltammetric cell 1. A feeding unit 5 is connected to the voltammetric cell 1. The current sampler device 4 is coupled via amplifier 6 to an indicating device 7 and to a recording or registering device 8. An integrator 9 is also connected to the indicator 7.

In the apparatus according to the invention the pump 2 delivers liquid pulsatingly into the voltammetric cell 1. At the same time the pump 2 controls the current sampler 4 via the time delay relay 3 such that the current sampler takes current only during the time when the flow rate or velocity of liquid delivered by the pump has attained 50% of its maximum and is increasing towards the maximum, and after attaining the maximum decreases to 50% of the maximum. In the time period when the flow rate has achieved or attained 50% of the maximum flow rate and continues to decrease towards a minimum the time delaying relay 3 stops the current sampler 4. The current sampler 4 passes the signal via the amplifier 6 to the indicator 7 and registering or recording device 8.

As can be seen from FIG. 2 the distance between the measurement electrode 11 and the restriction in the liquid inlet must be adjusted such that the cross-section of the liquid jet D should be greater in the region of the electrode than the measurement surface $d$ of the electrode. Bearing in mind that the electrode surface area $d$ is given, while the flow rate of the liquid depends on the pump delivery and the cross-section of the restriction, the above-specified condition can be ensured by adjustment of the spacing of the restriction and the electrode.

Proceeding as described in accordance with the invention it has been possible to increase the sensitivity of measurement by an order of magnitude.

We claim as our invention:

1. A process for voltammetric measurement of sample component quantities in a liquid comprising the steps of:

pulsatingly conveying said liquid as a jet of liquid flow along a path substantially perpendicular to and into contact with a voltametric electrode surface whereby a voltametric current is produced;

adjusting the cross section of the jet of liquid flow so that said cross section is greater than the measurement surface of the electrode in the region of the electrode surface;

sampling the produced voltametric current only during that time period from when said jet of liquid flow has attained at least 50% of its maximum velocity, as it increases towards said maximum velocity, and, after attaining the maximum velocity until the velocity decreases to 50% of said maximum velocity;

integrating the sampled current signal and determining said component quantities therefrom.

2. Apparatus for voltametric measurement of sample component quantities in a liquid comprising:

a voltametric measuring cell containing a measurement electrode;

delivery means for conveying said liquid, as a pulsating jet of liquid flow, into contact with the surface of said electrode whereby a current is generated which changes as a function of the flow rate of said jet of liquid;

means for adjusting the cross section of said jet of liquid so that said cross section is greater than the measurement surface of the electrode in the region of the electrode surface;

means for maintaining the path of said liquid jet substantially perpendicular to the planar surface of the electrode;

time delay means electrically connected to said delivery means; current sampler means electrically connected to said time delay means and said voltametric cell;

said current sampler means being adapted to sample the produced voltametric current signal only during that time period from when the jet of liquid flow has attained at least 50% of its maximum velocity, as it increases toward said maximum velocity, and, after attaining said maximum velocity, until it decreases to 50% of said maximum velocity; and P1 means for integrating the sampled signal and determining the material quantities from the integrated data.

3. The apparatus, as claimed in claim 2, wherein said means for adjusting the cross section is a restriction in a liquid inlet to said cell and means for adjusting the spacing of said restriction and the electrode surface.

* * * * *